US011701321B2

United States Patent
Scheele et al.

(10) Patent No.: US 11,701,321 B2
(45) Date of Patent: *Jul. 18, 2023

(54) SOLID HAIR COSMETIC COMPOSITION

(71) Applicant: Henkel AG & Co. KGaA, Duesseldorf (DE)

(72) Inventors: Soeren Scheele, Pinneberg (DE); Manuela Mette, Kleinfeld (DE); Petra Westphal, Neu Wulmstorf (DE); Thomas Schroeder, Hamburg (DE)

(73) Assignee: HENKEL AG & CO. KGAA, Duesseldorf (DE)

( * ) Notice: Subject to any disclaimer, the term of this patent is extended or adjusted under 35 U.S.C. 154(b) by 147 days.

This patent is subject to a terminal disclaimer.

(21) Appl. No.: 16/926,386

(22) Filed: Jul. 10, 2020

(65) Prior Publication Data
US 2021/0007961 A1 Jan. 14, 2021

(30) Foreign Application Priority Data
Jul. 10, 2019 (DE) .................. 10 2019 210 160.7

(51) Int. Cl.
| | |
|---|---|
| *A61K 8/73* | (2006.01) |
| *A61K 8/362* | (2006.01) |
| *A61K 8/41* | (2006.01) |
| *A61K 8/34* | (2006.01) |
| *A61K 8/02* | (2006.01) |
| *A61Q 5/12* | (2006.01) |
| *B29C 39/00* | (2006.01) |
| *A61K 8/36* | (2006.01) |
| *B29K 105/00* | (2006.01) |
| *B29L 31/00* | (2006.01) |

(52) U.S. Cl.
CPC ............ *A61K 8/732* (2013.01); *A61K 8/0229* (2013.01); *A61K 8/342* (2013.01); *A61K 8/345* (2013.01); *A61K 8/361* (2013.01); *A61K 8/362* (2013.01); *A61K 8/416* (2013.01); *A61Q 5/12* (2013.01); *B29C 39/003* (2013.01); *B29K 2005/00* (2013.01); *B29K 2105/0005* (2013.01); *B29L 2031/718* (2013.01)

(58) Field of Classification Search
CPC ........ A61K 8/361; A61K 8/732; A61K 8/416; A61K 8/0229; A61K 8/345; A61K 8/362; A61K 8/73; A61K 8/342; A61K 2800/5922; A61Q 5/12; B29C 39/003; B29C 39/02; B29L 2031/718; B29K 2005/00; B29K 2003/00; B29K 2105/0005
See application file for complete search history.

(56) References Cited

U.S. PATENT DOCUMENTS

| | | | |
|---|---|---|---|
| 5,824,629 A | 10/1998 | Petritsch | |
| 2006/0034793 A1* | 2/2006 | Yerby | .................. A61K 8/046 424/70.19 |
| 2006/0228319 A1 | 10/2006 | Vona, Jr. et al. | |
| 2015/0013712 A1* | 1/2015 | Ishii | ........................ A61Q 5/06 264/123 |
| 2015/0111802 A1* | 4/2015 | Constantine | .......... A61K 8/463 510/130 |
| 2016/0317396 A1* | 11/2016 | Perfitt | .................... A45D 33/02 |
| 2018/0289608 A1 | 10/2018 | Constantine et al. | |

FOREIGN PATENT DOCUMENTS

| | | | |
|---|---|---|---|
| EP | 1712258 A1 | 10/2006 | |
| FR | 3053888 A1 | 1/2018 | |
| FR | 3068243 A1 | 1/2019 | |
| GB | 2537649 A | * 10/2016 | .......... A61K 8/0208 |
| KR | 101965607 B1 | 4/2019 | |
| WO | 9515745 A1 | 6/1995 | |
| WO | 2019/001940 A1 | 1/2019 | |
| WO | 2020/113484 A1 | 6/2020 | |

OTHER PUBLICATIONS

Schmitt in Chemistry and Technology of the Cosmetic and Toiletries Industry, 1st edition, 2012, pp. 16-17. (Year: 2012).*
Hasegawa Tae, (JP 2010229071 A, PE2E Trans). 2010 (Year: 2010).*
Konno Yoshihiro et al., KR 20170076809 A, PE2E Eng. Translation, 2017. (Year: 2017).*

* cited by examiner

*Primary Examiner* — Blessing M Fubara
(74) *Attorney, Agent, or Firm* — Lorenz & Kopf, LLP

(57) ABSTRACT

The present disclosure relates to a solid hair cosmetic composition comprising—based on the total weight of the cosmetic composition—0.1 to 40.0% by weight of at least one polysaccharide, at least one polysaccharide being starch from corn, rice, potato or tapioca; modified starch; hydroxypropyl starch phosphate or a dextrin, and optionally: 10.0 to 60.0% by weight of at least one polyhydric alcohol, 0.1 to 15.0% by weight of at least one cationic surfactant, and 0.1 to 15.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid, as well as production and application methods and uses thereof.

19 Claims, No Drawings

SOLID HAIR COSMETIC COMPOSITION

CROSS-REFERENCE TO RELATED APPLICATION

This application claims priority to German Patent Application No. 10 2019 210 160.7, filed Jul. 10, 2019, which is incorporated herein by reference in its entirety.

TECHNICAL FIELD

The technical field is directed to solid cosmetic compositions based on specific polysaccharides, in particular solid conditioner compositions which dissolve and foam in contact with water. The solid cosmetic compositions possibly include other ingredients such as surfactants, specific polyols, fatty alcohols and/or fatty acid(s). The technical field is further directed to processes for the preparation of solid cosmetic compositions and their use for conditioning mainly human hair, but also the skin of the human body.

BACKGROUND

Surfactant-containing products for conditioning primarily human hair, but also the skin of the human body, have been known for a long time and are offered on the market mainly in liquid or paste form in suitable packaging. End users take the required amount of product from the packaging during use and dispose of it after emptying. Compared to certain conditioners sold in solid form, such products offer the user the advantage of easy and quick handling, which is why they dominate the market today. However, this advantage is achieved by accepting certain disadvantages, which are discussed below. In most cases, the packaging of the described products in liquid or paste form includes non-recyclable plastic, which is a serious problem from an environmental point of view in view of the constantly growing amount of plastic waste.

Another problem is that previous products usually contain higher quantities of water or water/solvent mixtures, which means that the products have a larger volume and, possibly of greater importance from a transport point of view, a relatively high weight. This is disadvantageous for several reasons. In times of increasing water scarcity, resources should be saved. An undesirable, increased transport volume associated with large-volume heavy products is also important from an environmental and cost perspective. Another interesting point is that worldwide travel activity is constantly increasing. Consumers are therefore increasingly interested in cosmetic products that are easy to transport due to their low weight and volume. This is particularly relevant with regard to air travel, as larger containers containing liquids are generally excluded from being carried in an aircraft cabin, so that a passenger travelling only with hand luggage often finds himself in the situation, due to the cosmetics products that dominate the market today, of not being able to take his preferred product selection with him or having to decant the corresponding products into smaller containers first, which, however, is generally accompanied by an even greater volume of packaging material.

The provision of alternative product forms with lower water content, contained in space-saving, more environmentally friendly, for example recyclable, packaging, is therefore an important objective in the formulation of improved, contemporary and sustainable cosmetic products.

Fixed conditioner compositions have been known for some time and occupy a market niche. Although they have a very low water or solvent content in general and are often packaged with little material, many people find them uncomfortable to handle because an incipient piece of conditioner is difficult to transport, often partially dissolves when placed near a shower or bathtub or next to the sink, which is also inefficient, and makes the sink or other storage location look unattractive due to conditioner residue, and because conditioner pieces have a tendency to slip out of the user's hand.

Another disadvantage with known solid conditioner formulations, especially with rather small conditioner pieces, is that it takes some time for enough of the conditioner piece to dissolve to achieve the desired amount of foam and the desired conditioning effect. On the one hand, this is usually undesirable for users because of the additional time required, and on the other hand it can be associated with higher water consumption for personal hygiene, as many users do not turn off the water flow of the shower or tap during conditioning. From this point of view, it does not make sense to market known conditioner formulations, especially in miniaturized form of a known piece of conditioner, as their dissolution is too slow as the formulations of these conditioners are not optimized for marketing in single application portions.

BRIEF SUMMARY

Solid hair cosmetic compositions, processes for preparing the same, and processes for treating hair using the same are provided herein. In an embodiment, a solid hair cosmetic composition includes—based on the total weight of the cosmetic composition—
  a) from about 0.1 to about 40.0% by weight of at least one polysaccharide, wherein at least one polysaccharide is starch from corn, rice, potato or tapioca; modified starch; and/or a dextrin, and optionally:
  b) from about 10.0 to about 60.0% by weight of at least one polyhydric alcohol,
  c) from about 0.1 to about 15.0% by weight of at least one cationic surfactant, and from about 0.1 to about 15.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In view of the problems and requirements described above, formulations and manufacturing processes suitable for solid cosmetic conditioning agents are provided which, by their nature, can be packaged in individual application portions, as well as processes for their manufacture and uses. Several measures have been established that can contribute to this suitability. Thus, the task of the present disclosure is solved by the formulation of procedures and uses described in detail below:

The present disclosure is exemplified by:
1. A solid hair cosmetic composition comprising—based on the total weight of the cosmetic composition— a. from about 0.1 to about 40.0 by weight of at least one polysaccharide, wherein at least one polysaccharide is starch from corn, rice, potato or tapioca; modified starch; or a dextrin, and optionally:
b. from about 10.0 to about 60.0% by weight of at least one polyhydric alcohol,
c. from about 0.1 to about 15.0% by weight of at least one cationic surfactant, and
d. from about 0.1 to about 15.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

2. A solid hair cosmetic composition according to point 1, comprising—based on the total weight of the cosmetic composition—
a. from about 0.1 to about 40.% by weight of at least one polysaccharide, wherein at least one polysaccharide is starch from corn, rice, potato or tapioca; modified starch; or a dextrin,
b. from about 10.0 to about 60.0% by weight of at least one polyhydric alcohol,
c. from about 0.1 to about 15.0% by weight of at least one cationic surfactant, and
d. from about 0.1 to about 15.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

3. A solid hair cosmetic composition according to any of the foregoing, wherein the polysaccharide a) contains a corn starch.

4. A solid hair cosmetic composition according to any of the foregoing, wherein the polysaccharide a) contains a dextrin.

5. A solid hair cosmetic composition as defined in point 4, where the dextrin is maltodextrin.

6. A solid hair cosmetic composition according to any of the foregoing, wherein the polysaccharide a) contains a modified starch.

7. A solid hair cosmetic composition according to point 6, wherein the modified starch is hydroxypropyl starch phosphate.

8. A solid hair cosmetic composition according to any of the foregoing, wherein the polysaccharide a) contains or consists of a corn starch, a dextrin and/or a modified polysaccharide.

9. A solid hair cosmetic composition according to any of the foregoing, wherein the polysaccharide a) contains or consists of a corn starch and maltodextrin.

10. A solid hair cosmetic composition according to any of points 1 to 8, wherein the polysaccharide a) contains or consists of corn starch, maltodextrin and hydroxypropyl starch phosphate.

11. A solid hair cosmetic composition according to any of the foregoing, where the maize starch is *Zea Mays* (corn) starch.

12. A solid hair cosmetic composition according to any of the preceding points, comprising from about 1 to about 30.0% by weight of at least one polysaccharide Hair cosmetic composition a), preferably from about 5 to about 25% by weight and more preferably from about 10 to about 25% by weight (based on the total weight of the cosmetic composition).

13. A solid hair cosmetic composition according to any of the foregoing, comprising glycerol as polyhydric alcohol b).

14. A solid hair cosmetic composition according to any of the preceding points, comprising from about 10 to about 50% by weight of at least one polyhydric alcohol b), preferably from about 20 to about 40% by weight and more preferably from about 25 to about 35% by weight (based on the total weight of the cosmetic composition).

15. A solid hair cosmetic composition according to any of the foregoing, comprising as cationic surfactant c) at least one compound from the following group of the:
i. Alkylquats,
ii. Esterquats,
iii. quaternary imidazolines,
iv. Amidoamines and/or cationized Amidoamines and
v. Mixtures of these.

16. A solid hair cosmetic composition according to any of the preceding points, comprising at least one cationic surfactant c) from group i, preferably $C_8$-$C_{30}$ alkyl tri-$C_1$-$C_4$ alkylammonium salts, more preferably lauryl trimethylammonium salts, Cetyltrimethylammonium salts, stearyltrimethylammonium salts, Behentrimethylammonium salts and/or mixtures thereof, and in particular cationic surfactant salts known under the INCI designation "cetrimonium" and/or "behentrimonium".

17. A solid hair cosmetic composition according to any of the preceding points, comprising from about 0.5 to about 10% by weight of at least one cationic surfactant c), preferably from 0.5 to 5% and more preferably from about 1 to about 4% by weight (based on the total weight of the cosmetic composition).

18. A solid hair cosmetic composition according to any of the preceding points, comprising as component d) at least one saturated or unsaturated, branched or unbranched C8-C30 alcohol, in particular cetyl alcohol, stearyl alcohol, or mixtures thereof.

19. A solid hair cosmetic composition according to one of the preceding points, comprising as component d) saturated or unsaturated, branched or unbranched $C_8$-$C_{30}$ carboxylic acids and/or their salts, preferably $C_{10}$-$C_{22}$ carboxylic acids and/or their salts and in particular coco acids, lauric acid, myristic acid, palmitic acid, stearic acid, behenic acid, oleic acid as well as mixtures thereof and/or the salts of these acids.

20. A solid hair cosmetic composition according to any of the preceding points, comprising as component d) palmitic acid and/or stearic acid and mixtures thereof, and/or cetyl alcohol and/or stearyl alcohol.

21. A solid hair cosmetic composition according to any of the foregoing, comprising as component d) palmitic acid, stearic acid and cetyl alcohol.

22. A solid hair cosmetic composition according to any of the foregoing, comprising from about 0.5 to about 15%, preferably from about 2 to about 15% and more preferably from about 5 to about 12% by weight of component d) (based on the total weight of the cosmetic composition).

23. A solid hair cosmetic composition according to any of the foregoing, further comprising, based on the total weight of the cosmetic composition, from about 0.01 to about 5.00% by weight of at least one cationic polymer, preferably at least one cationic polysaccharide polymer obtainable from guar, *cassia* and/or inulin.

24. A solid hair cosmetic composition according to any of the foregoing, further comprising—based on the total weight of the cosmetic composition—from about 0.001 to about 0.01% by weight of at least one bittering agent, preferably a compound known under the INCI designation denatonium benzoate.

25. A solid hair cosmetic composition according to any of the preceding points, further comprising—based on the total weight of the cosmetic composition—from about 0.01 to about 10.0% by weight of at least one oil, fat and/or wax component, preferably a naturally occurring oil, fat or wax.

26. A solid hair cosmetic composition according to any of the previous points, further comprising one or more vegetable oils and/or one or more vegetable butters.

27. A solid hair cosmetic composition according to point 26, containing Shea Butter (INCI designation: *Butyrospermum parkii* (Shea) Butter).

28. A solid hair cosmetic composition according to one of points 26 or 27, containing apricot kernel oil, argan oil, jojoba oil, marula oil, almond oil, olive oil, coconut oil and/or sunflower oil.

29. A solid hair cosmetic composition according to any of the preceding points, further comprising one or more plant extracts.

30. A solid hair cosmetic composition according to any of the foregoing, further comprising citric acid, lactic acid, malic acid and/or glycolic acid, especially citric acid and/or lactic acid.

31. A solid hair cosmetic composition according to any of the foregoing, further comprising sodium bicarbonate.

32. A solid hair cosmetic composition according to any of the foregoing comprising water in an amount up to 25% by weight (based on the weight of the composition).

33. A solid hair cosmetic composition according to one of the previous points in the form of a pen or piece.

34. A solid hair cosmetic composition according to point 33 in the form of a stick.

35. A solid hair cosmetic composition as defined in point 34, with a Shore AO hardness value of from about 5 to about 20.

36. A solid hair cosmetic composition as defined in point 35, with a Shore AO hardness value of from about 5 to about 15.

37. A solid hair cosmetic composition according to any one of points 34 to 36 comprising water in an amount up to 25% by weight, preferably about 20% and more preferably about 15% by weight (based on the weight of the composition).

38. A solid hair cosmetic composition according to point 33 in the form of a multiple use piece.

39. A solid hair cosmetic composition as defined in point 33 in the form of a single use piece.

40. A solid hair cosmetic composition as defined in point 39, with a Shore AO hardness value of from about 15 to 35.

41. A solid hair cosmetic composition as defined in point 40, with a Shore AO hardness value of from about 20 to about 30.

42. A solid hair cosmetic composition according to any of the preceding points for the cleansing and/or care of human skin and/or human hair.

43. A solid hair cosmetic composition according to one of the preceding points in the form of a conditioning agent.

44. A solid hair cosmetic composition according to any of the preceding points for use after hair cleansing as a leave-on or rinse-off composition.

45. A process for preparing the solid hair conditioning composition according to any of the foregoing, comprising the process:
a. Mix all ingredients with sufficient heat and agitation to ensure that all ingredients are melted and/or evenly distributed,
b. Allow the resulting mixture to cool and solidify.

46. A process for preparing the solid hair conditioning composition according to any one of points 1 to 44, comprising the process:
a. Mix all ingredients with sufficient heat and agitation to ensure that all ingredients are melted and/or evenly distributed,
b. Pour the resulting mixture into a pin/piece mould,
c. Allow the mixture to cool and solidify.

47. A process for preparing the solid hair conditioning composition according to any one of points 1 to 44, comprising the process:
a. Mix all ingredients with sufficient heat and agitation to ensure that all ingredients are melted and/or evenly distributed,
b. Pour the resulting mixture into a mould,
c. Allow the mixture to cool and solidify.

48. method for treating hair, preferably conditioning hair, in which a solid hair cosmetic composition is mixed with water according to one of points 1 to 44 and applied to the hair or in which a stick or piece is applied directly to wet hair and an incorporation takes place.

49. The use of a solid hair cosmetic composition according to any one of points 1 to 44 for treating, preferably conditioning and/or conditioning the hair.

50. A solid hair cosmetic composition prepared by a method according to one of the definitions of points 45 to 48.

The present disclosure thus concerns a solid hair cosmetic composition comprising—based on the total weight of the cosmetic composition—
a) from about 0.1 to about 40.0% by weight of at least one polysaccharide, wherein at least one polysaccharide is starch from corn, rice, potato or tapioca; modified starch; hydroxypropyl starch phosphate or a dextrin, and optionally:
b) from about 10.0 to about 60.0% by weight of at least one polyhydric alcohol,
c) from about 0.1 to about 15.0% by weight of at least one cationic surfactant, and
d) from about 0.1 to about 15.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

Such a formulation offers the right properties for single application portions, especially with regard to their dissolving and foaming behaviour during use.

The present disclosure further relates to a solid hair cosmetic composition as described above, comprising—based on the total weight of the cosmetic composition—
a) from about 0.1 to about 40.0% by weight of at least one polysaccharide, wherein at least one polysaccharide is starch from corn, rice, potato or tapioca; modified starch; or a dextrin,
b) from about 10.0 to about 60.0% by weight of at least one polyhydric alcohol,
c) from about 0.1 to about 15.0% by weight of at least one cationic surfactant, and
d) from about 0.1 to about 15.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

The compositions according to the present disclosure are solid at about 25° C. Solid compositions within the meaning of the present application are three-dimensional, dimensionally stable entities which are not liquid or gaseous, that is to say, which retain their external shape even without a surrounding vessel. However, the term "solid" does not imply anything about density or elasticity or other physical properties, so that jellies, brawn, butter etc. can also be solid as contemplated herein as long as they are dimensionally stable at 25° C.

Such a formulation offers the right properties for single application portions, especially with regard to their dissolving behaviour during use. The high concentrations of the active substances in such a composition are associated with the advantages that few resources are consumed during production and transport and that the products, even after they have reached the hands of a consumer via the trade, can be easily transported without great effort or restrictions, whether to the gym or on a flight.

The present disclosure further relates to a solid hair cosmetic composition as previously described, comprising at least one polysaccharide starch from corn, rice, potato or tapioca; modified starch; or a dextrin.

The solid hair cosmetic composition comprises preferably:
at least one starch obtained from natural sources (preferably where the starch obtained from natural sources is preferably from maize, rice, potato or tapioca),
at least one modified starch, and/or
at least one dextrin.

The present disclosure also relates to a solid hair cosmetic composition as described above, containing as polysaccharide a)
i. Starch fractions from maize and/or
ii. modified starches and/or
iii. Derivatives of dextrins.

Especially preferred is a solid hair cosmetic composition, as described above, containing as polysaccharide a)(i) starch fractions from maize.

Also particularly preferred is a solid hair cosmetic composition, as described above, containing compounds known as polysaccharide a) ii. under the INCI designation Hydroxypropyl Starch Phosphates.

Also particularly preferred is a solid hair cosmetic composition, as described above, containing as polysaccharide a) iii. Maltodextrin.

Especially preferred is a solid hair cosmetic composition, as described above, containing polysaccharides a) from groups i, ii and iii, preferably starch fractions from maize, compounds known under the INCI designation Hydroxypropyl Starch Phosphates and maltodextrin.

These polysaccharides have proved to be well suited as stabilising agents in the context of the present disclosure claimed here. Their use makes it possible to provide ready-made consumer products that retain their properties and appearance over a long period of time and under various environmental conditions.

The present disclosure further relates to a solid hair cosmetic composition as described above, comprising (based on the total weight of the cosmetic composition):
a) from about 10.0 to about 60.0% by weight of at least one polyhydric alcohol, Polyhydric alcohols are mostly well tolerated by the skin and as solvents they ensure that the solid cosmetic compositions available with them are not too solid or too difficult or slow to dissolve. These advantageous properties are particularly evident with glycerine.

The present disclosure also relates to a solid hair cosmetic composition as described above, containing as polyhydric alcohol b) alditols such as mannitol, isomalt, lactitol, sorbitol and xylitol, threit, erythritol and arabitol, 1,2-propylene glycol, 1,3-butylene glycol, dipropylene glycol, glycerol and/or diglycerol, preferably glycerol. According to the present disclosure, compositions preferably contain glycerol in the quantities mentioned above.

The present disclosure further relates to a solid hair cosmetic composition as described above, comprising glycerol as polyhydric alcohol b).

The present disclosure further relates to a solid hair cosmetic composition as described above, preferably comprehensive (based on the total weight of the cosmetic composition):
bi) from about 20.0 to about 60.0% by weight of at least one polyhydric alcohol, in particular more than from about 30.0 to about 60.0% by weight of at least one polyhydric alcohol, preferably from about 32.0 to about 50.0% by weight of at least one polyhydric alcohol.

In the defined concentration range, the advantageous properties described above become even more apparent.

The present disclosure further relates to a solid hair cosmetic composition as described above, comprising (based on the total weight of the cosmetic composition):
b) from about 0.1 to about 15.0% by weight of at least one cationic surfactant, Cationic surfactants carry a positive charge in their hydrophilic part. This positive charge causes the surfactant molecules to attach themselves to the negatively charged skin and hair surface. In this way they neutralize the charge, prevent the hair from flying, have a smoothing effect, increase hair shine and improve wet comb-ability. They are primarily used in conditioners, hair conditioners and hair treatments, rarely in shampoos. In addition, cationic surfactants have a co-conserving effect in cosmetic products due to their bactericidal effect, i.e. an inhibiting effect on bacteria.

In principle, all cationic surface-active substances suitable for use on the human body are suitable as cationic surfactants in compositions according to the present disclosure. These are exemplified by at least one water-solubilizing, cationic group, such as a quaternary ammonium group, or by at least one water-solubilizing, cationizable group, such as an amine group and furthermore at least one lipophilic alkyl group with about 6 to 30 C atoms, or also by at least one imidazole group or at least one imidazylalkyl group.

In general, cationic surfactants are divided into groups according to their structural characteristics. Particularly suitable for use in the compositions according to the present disclosure are cationic surfactants a) from at least one of the groups of alkylquats, esterquats, quaternary imidazolines, amidoamines and/or cationized amidoamines.

The present disclosure further relates to a solid hair cosmetic composition as previously described, comprising as cationic surfactant a) at least one compound from the following group of the:
i. Alkylquats,
ii. Esterquats,
iii. quaternary imidazolines,
iv. Amidoamines and/or cationized Amidoamines and
v. Mixtures of these.

These specifically named cationic surfactants have shown a conditioning effect in the compositions according to the present disclosure which is perceived as particularly pleasant.

Especially preferred compositions according to the present disclosure contain as cationic surfactants c)
quaternary ammonium compounds (alkylquats) with at least one $C_8$-$C_{24}$ alkyl radical,
Esterquats and
Amidoamines each having at least one $C_8$-$C_{24}$ acyl group and mixtures thereof.

Quaternary ammonium compounds with at least one $C_8$-$C_{24}$ alkyl radical are particularly preferred ammonium halides, especially chlorides, and ammonium alkyl sulphates, such as methosulphates or ethosulphates, such as $C_8$-$C_{24}$ alkyl trimethylammonium chlorides, $C_8$-$C_{24}$ dialkyldimethylammonium chlorides and $C_8$-$C_{24}$ trialkylmethylammonium chlorides, e.g. cetyltrimethylammonium chloride, stearyltrimethylammonium chloride, distearyldimethylammonium chloride, lauryldimethylammonium chloride, lauryldimethylbenzylammonium chloride and tricetylmethylammonium chloride, as well as the imidazolium compounds known under the INCI designations Quaternium-27, Quaternium-83, Quaternium-87 and Quaternium-91. The alkyl chains of the surfactants mentioned above preferably have 8 to 24 carbon atoms.

Esterquats are cationic surfactants which contain both at least one ester function and at least one quaternary ammonium group as a structural element and furthermore at least one $C_8$-$C_{24}$ alkyl radical or $C_8$-$C_{24}$ acyl radical. Preferred esterquats are quaternized ester salts of fatty acids with triethanolamine, quaternized ester salts of fatty acids with diethanolalkylamines and quaternized ester salts of fatty acids with 1,2-dihydroxypropyl dialkylamines. Such products are sold under the trademarks Stepantex®, Dehyquart® and Armocare®. N,N-bis(2-palmitoyloxyethyl)dimethylammonium chloride, distearoylethyl dimonium methosulfates and distearoylethyl hydroxyethylmonium methosulfates are preferred examples of such esterquats.

The alkylamidoamines are usually produced by amidation of natural or synthetic $C_8$-$C_{24}$ fatty acids and fatty acid sections with di-($C_1$-$C_3$)alkylaminoamines. Compounds from this substance group which are particularly suitable according to the present disclosure are for example the compounds known under the INCI designations stearamidopropyl dimethylamine, behenamidopropyl dimethylamine and/or brassicamidopropyl dimethylamine. Stearamidopropyl dimethylamine is particularly preferred.

Alkylamidoamines are usually produced by amidation of natural or synthetic C8-C24 fatty acids and fatty acid sections with di-(C1-C3)alkylaminoamines. A compound from this substance group which is particularly suitable according to the present disclosure is stearamidopropyldimethylamine.

The present disclosure further relates to a solid hair cosmetic composition as described above, comprising at least one cationic surfactant c) from group iii, in particular quaternium-87.

The present disclosure further relates to a solid hair cosmetic composition as described above, comprising at least one cationic surfactant b) from group i, preferably $C_8$-$C_{30}$ alkyl tri-$C_1$-$C_4$ alkylammonium salts and in particular cationic surfactant salts known under the INCI designation "Cetrimonium" and/or "Behentrimonium".

These specifically named cationic surfactant salts have shown in the compositions according to the present disclosure a conditioning effect which is perceived as particularly pleasant.

Compositions preferred according to the present disclosure contain at least one cationic surfactant in a total amount of from about 0.1 to about 15% by weight, preferably from about 2 to 10 about % by weight, particularly preferably from about 4 to about 8% by weight, each based on the weight of the composition.

In addition to conditioning agents, the compositions according to the present disclosure can also be cleaning agents. Also contains cleaning agents preferred according to the present disclosure— contains at least one cationic surfactant, preferably in a total amount of from about 0.1 to about 2% by weight, more preferably from about 0.2 to about 1% by weight and particularly preferably from about 0.3 to about 0.5% by weight, each based on the weight of the composition, and at least one further surfactant selected from anionic, amphoteric, zwitterionic and/or non-ionic surfactants, preferably in a total amount of from about 1 to about 40% by weight, more preferably from about 2 to about 35% by weight and particularly preferably from about 3 to about 30% by weight, each based on the weight of the composition.

The present disclosure further relates to a solid hair cosmetic composition as described above, comprising (based on the total weight of the cosmetic composition):
c) from about 0.1 to about 15.0.% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

The present disclosure further relates to a solid hair cosmetic composition as described above, comprising as component d) at least one saturated or unsaturated, branched or unbranched C8-C30 alcohol, in particular cetyl alcohol, stearyl alcohol, or mixtures thereof.

These compounds have proved to be particularly suitable structure-giving ingredients for the purposes of the present disclosure. They can be used to formulate hair cosmetic compositions of sufficient strength that do not melt too low.

The present disclosure further relates to a solid hair cosmetic composition as described above, comprising as component d) saturated or unsaturated, branched or unbranched C8-C30 carboxylic acids and/or their salts preferably C10-C22 carboxylic acids and/or their salts and in particular coco acids, lauric acid, myristic acid, palmitic acid, stearic acid, behenic acid, oleic acid as well as mixtures thereof and/or the salts of these acids in the amounts described above.

Such a composition has essentially comparable advantages to those previously described in connection with $C_8$-$C_{30}$ alcohols.

The present disclosure further relates to a solid hair cosmetic composition as previously described, further comprising—based on the total weight of the cosmetic composition—from about 0.01 to about 5.00% by weight of at least one cationic polymer, preferably at least one cationic polysaccharide polymer obtainable from guar, *cassia* and/or inulin.

Compositions preferred according to the present disclosure contain at least one saturated or unsaturated, branched or unbranched C8-C30 alcohol and/or a saturated or unsaturated, branched or unbranched C8-C30 carboxylic acid and/or a salt of a saturated or unsaturated, branched or unbranched C8-C30 carboxylic acid in a total amount of from about 0.1 to about 20% by weight, preferably from about 1 to about 18% by weight, particularly preferably from about 4 to about 15% by weight, in particular from about 6 to about 14% by weight; in each case based on the weight of the composition.

The present disclosure further relates to a solid hair cosmetic composition as previously described, further comprising—based on the total weight of the cosmetic composition—from about 0.01 to about 5.00% by weight of at least one cationic polymer, preferably at least one cationic polysaccharide polymer obtainable from guar, *cassia* and/or inulin.

Cationic polymers have conditioning properties, i.e. they provide a pleasant skin or hair feel and thus offer added value. They can be used in the context of the present disclosure without significantly affecting the cleaning performance. The specifically named polymers are particularly suitable.

In more detail, suitable cationic care polymers are also to be understood, for example:
quaternized cellulose polymers, especially polyquaternium-10, as commercially available under the names Celquat® and Polymer JR®,
hydrophobically modified cellulose derivatives, for example the cationic polymers sold under the trade name SoftCat®, cationic alkyl polyglycosides,
cationized honey, for example the commercial product Honeyquat® 50,
cationic guar derivatives, in particular those marketed under the trade names CosmediaGuar, N-Hance® and Jaguar® distributed products,
polymeric dimethyldiallylammonium salts and their copolymers with esters and amides of acrylic acid and methacrylic acid, especially polyquaternium-6 and polyquaternium-7. The products commercially available under the names Merquat® 100 (poly(dimethyldiallylammonium chloride)) and Merquat®550 (Dimethyldiallylammonium chloride-acrylamide copolymer) are examples of such cationic polymers,
Copolymers of vinylpyrrolidone with quaternized derivatives of dialkylaminoalkyl acrylate and -methacrylate, such as those quaternized with diethyl sulphate Vinylpyrrolidon-Dimethylaminoethylmethacrylat-Copolymere. Such compounds are commercially available under the names Gafquat®734 and Gafquat®755,
Vinylpyrrolidone-vinylimidazolium methochloride copolymers, as offered under the names Luviquat® FC 370, FC 550, FC 905 and HM 552,
quaternized polyvinyl alcohol,
and the products listed under the designations Polyquaternium 2, Polyquaternium 17, Polyquaternium 18, Polyquaternium-24, Polyquaternium 27, Polyquaternium-32, Polyquaternium-37, Polyquaternium 74 and Polyquaternium 89 known polymers.

Particularly preferred cationic polymers are quaternized cellulose polymers, hydrophobically modified quaternized cellulose polymers, cationic guar derivatives and/or cationic polymers based on acrylic acid (derivative), which are particularly preferably selected from the polymers known under the INCI designations guar hydroxypropyltrimonium chlorides, polyquaternium-6, polyquaternium-7, polyquaternium-10, polyquaternium-37 and/or polyquaternium-67. Cationic polysaccharide polymers, especially guar hydroxypropyltrimonium chloride, are particularly preferred for the purposes of the present disclosure.

Furthermore, cationic polymers, which are obtained from natural sources (besides guar), such as a cationic inulin polymer, are particularly preferred. A content of these specific polymer types in the mixture of active ingredients according to the present disclosure is not only beneficial for the improvement of hair care properties, but it was also found that polymers in combination with other cationic polymers do not cause an over conditioning effect even after regular use.

Inulin is a polysaccharide belonging to the group of fructans. In addition to a terminal glucose building block, the chain contains up to 60 fructose monomers, each of which is linked via β-2,1-glycosidic bonds. Inulin may be obtained from the leaves, roots, fruits and/or flowers of composites and/or umbellifers, such as Jerusalem artichokes, chicory, artichokes and/or parsnips.

Cationic inulin polymers particularly suitable according to the present disclosure are cationically modified by reacting hydroxyl groups of the fructose building blocks with reactive quaternary ammonium compounds. Suitable quaternary ammonium compounds are preferably compounds of the following formula $$N^+(R^1R^2R^3R^4)X^-$$

in which $R^1$, $R^2$ and $R^3$ are methyl or ethyl groups and $R^4$ is an epoxy-$R^5$—or a halohydrin group Y—$CH_2$—CH(OH)—$R^5$—, in which $R^5$ is a $C_1$-$C_3$ alkylene group, Y is a halide and X is an anion such as Cl—, Br—, I— or HSO4. Particularly suitable cationic inulin polymers b) for the purposes of the present disclosure correspond to the formula $$R-O-CH_2-CH(OH)-R^5-N^+(R^1R^2R^3)X^-,$$

wherein R is inulin and the other residues have the same meaning as above.

In a particularly preferred embodiment, the compositions according to the present disclosure contain cationic inulin polymers cationically modified with cationic hydroxy-$C_1$-$C_3$-alkyl-trialkylammonium groups, in particular with hydroxypropyltrimethylammonium groups. Within this version, cationic inulin polymers known and commercially available under the INCI designation Hydroxypropyltrimonium Inulin are preferred.

The degree of cationic substitution of cationic inulin polymers, especially of cationic inulins known under the INCI designation Hydroxypropyltrimonium Inulin, can be varied and adjusted as required. For use in the cosmetic compositions according to the present disclosure, it has been shown to be particularly preferred when such cationically modified inulin polymers exhibit a higher degree of cationic modification (higher degree of cationic substitution), because this allows better coacervate formation and ultimately better care performance to be achieved in the compositions.

In a particularly preferred embodiment, the cationic inulin polymer contained in the cosmetic compositions according to the present disclosure has a cationic charge density about >1.5 meq/g, more preferably >about 2.0 meq/g, particularly preferably about >2.5 meq/g, very preferably about >3.0 meq/g and especially about >3.5 meq/g. Within this version it is particularly preferred if cationic inulin polymers known under the INCI designation Hydroxypropyltrimonium Inulin b) have a cationic charge density about >1.5 meq/g, more preferably about >2.0 meq/g, particularly preferably about >2.5 meq/g, very particularly preferably about >3.0 meq/g and particularly about >3.5 meq/g.

In another particularly preferred version, the cationic inulin polymer b) contained in the cosmetic compositions according to the present disclosure has an average molar mass of from about 2,000 to about 50,000 g/mol, more preferably from about 2,500 to about 40,000 g/mol, particularly preferably from about 3,000 to about 30,000 g/mol, very preferably from about 3,500 to about 20,000 g/mol and in particular from about 4,000 to about 10,000 g/mol. Within this version it is particularly preferred if cationic inulin polymers known under the INCI designation Hydroxypropyltrimonium Inulin b) have an average molar mass of from about 2,000 to 50,000 g/mol, more preferably from about 2,500 to about 40,000 g/mol, particularly preferably from about 3,000 to about 30,000 g/mol, very preferably from about 3,500 to about 20,000 g/mol and particularly 4 from about, 000 to about 10,000 g/mol.

The cationic inulin polymer(s)—preferably compounds known under the INCI designation Hydroxypropyltrimonium Inulin—are preferably used in the cosmetic cleansing compositions according to the present disclosure in an amount of from about 0.01 to about 5.00 wt.-%, more preferably from about 0.02 to about 4.00% by weight, particularly preferably from about 0.03 to about 3.00% by weight, very particularly preferably from about 0.04 to about 2.50% by weight and in particular from about 0.05 to about 2.00% by weight (based on the total weight of the cleansing compositions).

An optional component in the cosmetic compositions according to the present disclosure is another, cationic polymer. It was found that the combination of cationic inulin polymers and specific cationic polymers available from natural sources is particularly suitable for achieving particularly good hair care effects. Preferably, cationic polymers originating from natural sources are cationic polygalactomannan derivatives.

In another preferred embodiment, the cosmetic compositions of the present disclosure contain at least one other cationic polymer selected from cationic polymers of natural origin, preferably from cationic polygalactomannan derivatives.

Galactomannans are polysaccharides including combinations of mannose and galactose monomers in different contents. In it, the mannose units are connected to each other via ß(1-4)-glycosidic bonds; the galactose units via α(1-6)-bonds. The ratio of mannose to galactose monomers varies according to the type and origin of the plant and the temperature at which it was grown. In Greek fenugreek gum, the mannose-galactose ratio is about 1:1 (corresponding to one monomer of mannose to one monomer of galactose); in guar gum about 2:1; in tara gum about 3:1; in locust bean gum about 4:1 and in cassia gum about 5:1. All galactomannans from these sources are suitable for cationic modification and use as polymers in cosmetic compositions according to the present disclosure. Guar gum and/or cassia gum are particularly suitable for use in cosmetic products according to the present disclosure.

Like the cationic inulin polymers, the galactomannans, preferably galactomannans from the aforementioned sources, can be cationically modified by reacting the hydroxyl groups of the galactomannan polymers with reactive quaternary ammonium compounds. Suitable quaternary ammonium compounds are preferably compounds of the following formula

$N^+(R^1R^2R^3R^4)X^-$ in which $R^1$, $R^2$ and $R^3$ are methyl or ethyl groups and $R^4$ is an epoxy-$R^5$—or a halohydrin group Y—CH$_2$—CH(OH)—$R^5$—, in which $R^5$ is a $C_1$-$C_3$ alkylene group, Y is a halide and X is an anion such as Cl—, Br—, I— or HSO4. Particularly suitable cationic galactomannane polymers within the meaning of the present disclosure correspond to the formula

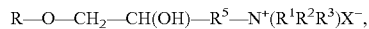
R—O—CH$_2$—CH(OH)—$R^5$—$N^+(R^1R^2R^3)X^-$, wherein R is the respective galactomannan and the other radicals have the same meaning as above.

In a particularly preferred embodiment, the compositions according to the present disclosure therefore contain cationic galactomannan polymers cationically modified with cationic hydroxy-$C_1$-$C_3$-alkyl-trialkylammonium groups, in particular with hydroxypropyltrimethylammonium groups. Within this version, galactomannan polymers which have been cationically modified with cationic hydroxy-$C_1$-$C_3$-alkyl-trialkylammonium groups, in particular with hydroxypropyltrimethylammonium groups, and which are derived from guar gum and/or cassia gum are particularly preferred.

In a particularly preferred form, the cosmetic compositions according to the present disclosure contain as cationic polymer c) at least one of the compounds known under the INCI designations Guar Hydroxypropyltrimonium Chloride, Hydroxypropyl Guar Hydroxypropyltrimonium Chloride and/or Cassia Hydroxypropyltrimonium Chloride.

Guar and Cassia polymers known under these INCI designations are commercially available from various suppliers, for example under the designations Jaguar®, N-Hance®, Polycare®, Clearhance®, Activsoft®, Guarquat®, VidaCare®. Jaguar® C-162, Jaguar® C500, Jaguar® Styl 100, N-Hance® 3196, N-Hance® HPCG 1000, Activsoft® C17, Guarquat® C130 KC, Guarquat® CP500 KC, Vida-Care® GHTC and/or Polycare® Split Therapy are specific examples of cationic polymers of natural origin that are particularly suitable according to the present disclosure.

Cationic polymers suitable according to the present disclosure are preferably used in the cosmetic compositions according to the present disclosure (based on their total weight) in amounts of from about 0.01 to about 2.00% by weight, more preferably from about 0.02 to about 0.90% by weight, particularly preferably from about 0.03 to about 0.80% by weight, very particularly preferably from about 0.04 to about 0.70% by weight and in particular from about 0.05 to about 0.60% by weight. Cationic galactomannan polymers, particularly preferably cationic galactomannan polymers originating from guar gum and/or cassia gum, and in particular compounds known under the INCI designations guar hydroxypropyltrimonium chloride, hydroxypropyl guar hydroxypropyltrimonium chloride and/or cassia hydroxypropyltrimonium chloride are used in the above-mentioned quantities in the compositions according to the present disclosure.

The present disclosure further relates to a solid hair cosmetic composition as described above, further comprising—based on the total weight of the cosmetic composition—from about 0.01 to about 20.0% by weight of at least one oil, fat and/or wax component, preferably a naturally occurring oil, fat or wax.

These are caring substances that help to keep both the skin and hair structure healthy. The defined concentration range makes it possible to use this care effect but at the same time to exclude noticeable greasiness after application of an appropriate composition. Naturally occurring raw materials have the advantage that they grow again and can therefore be used sustainably. This aspect is also becoming increasingly important to many users.

It has been found that vegetable butters with a melting range of from about 20° C. to about 35° C. are particularly suitable for incorporation into cosmetic compositions according to the present disclosure.

Accordingly, vegetable butters with a melting point in the range from about 20° C. to about 35° C., such as Shea butter (INCI designation), are particularly preferred: Butyrospermum parkii (Shea) Butter), Mango Butter (INCI designation: Mangifera indica (Mango) Seed Butter), Murumuru Butter (INCI designation: Astrocaryum Murumuru Seed Butter), cocoa butter (INCI designation: Theobroma cacao (Cocoa) Seed Butter) and/or Cupuacu Butter (INCI designation: Theobroma grandiflorum Seed Butter).

Cupuacu butter (INCI designation) is particularly preferred: Theobroma grandiflorum Seed Butter) and/or Shea Butter (INCI designation: Butyrospermum parkii (Shea)

Butter) and especially preferred is Shea Butter (INCI designation: *Butyrospermum parkii* (Shea) Butter).

The at least one vegetable butter (preferably Cupuacu butter and/or Shea butter; in particular shea butter) is used in the cosmetic compositions according to the present disclosure preferably in a proportion by weight of from about 0.01 to about 10.00% by weight, more preferably of from about 0.05 to about 5% by weight, particularly preferably of from about 0.10 to about 1% by weight of the total weight of the compositions.

Oils suitable according to the present disclosure are preferably perfume oils and/or vegetable triglyceride oils, such as coconut oil, (sweet) almond oil, walnut oil, peach kernel oil, apricot kernel oil, avocado oil, tea tree oil, soy bean oil, cotton seed oil, sesame oil, sunflower oil, tsubaki oil, evening primrose oil, rice bran oil, palm oil, Palm kernel oil, mango kernel oil, cranberry oil, sea buckthorn oil, meadow foam herb oil, thistle oil, macadamia nut oil, grape seed oil, amaranth seed oil, argan oil, bamboo oil, olive oil, Wheat germ oil, pumpkin seed oil, mallow oil, hazelnut oil, safflower oil, corn oil, olive oil, rapeseed oil, canola oil, sasanqua oil, jojoba oil, rambutan oil, marula oil and/or quinoa oil.

Particularly preferred are apricot kernel oil, argan oil, jojoba oil, marula oil, macadamia nut oil, pumpkin seed oil, amaranth seed oil, quinoa oil, soy bean oil, cotton seed oil, sunflower oil, palm oil, palm kernel oil, linseed oil, almond oil, corn oil, olive oil, rapeseed oil, sesame oil, soy bean oil, thistle oil, wheat germ oil, peach kernel oil, cranberry oil, sea buckthorn oil and/or coconut oil.

Especially preferred are apricot kernel oil, argan oil, jojoba oil, marula oil, almond oil, olive oil, coconut oil and/or sunflower oil.

The oil(s) can be used in the compositions according to the present disclosure preferably in a proportion by weight of from about 0.01 to about 10%, more preferably from about 0.05 to about 7%, more preferably from about 0.10 to about 5% by weight of the total weight of the compositions.

The present disclosure further relates to a solid hair cosmetic composition as previously described, further comprising—based on the total weight of the cosmetic composition—from about 0.001 to about 0.01% by weight of at least one bittering agent, preferably a compound known under the INCI designation Denatonium Benzoate.

A bitter substance is particularly important in cosmetics, household products etc. which are made up in such a way that their shape, colour, feel etc. appeal to small children or babies and encourage them to play, although swallowing could also occur. A bitter substance prevents this. Denatonium benzoate is an extremely strong bittering agent and is therefore particularly effective even at exceptionally low application concentrations. Furthermore, it is not associated with any known adverse effects.

In addition to the ingredients described above, the cosmetic compositions according to the present disclosure may contain at least one active ingredient advantageously selected from the group comprising plant extracts, humectants, protein hydrolysates, perfumes, UV filters, structurants such as maleic acid, dyes for colouring the composition, Active ingredients such as bisabolol and/or allantoin, antioxidants, preservatives such as sodium benzoate or salicylic acid, additional viscosity regulators such as salts (NaCl) or polymers, and pH adjusters such as α- and β-hydroxycarboxylic acids such as citric acid, lactic acid, malic acid, glycolic acid, and/or bases such as alkanolamines and/or sodium hydroxide).

Suitable plant extracts are extracts that can be produced from all parts of a plant. Usually these extracts are produced by extraction of the whole plant. However, in some cases it may be preferable to produce the extracts exclusively from flowers and/or leaves of the plant. Especially suitable are extracts from *Paeonia lactiflora, Rosa damascena* Flower, *Malus domestica* Fruit, *Argania spinosa* Shell Powder, *Laminaria saccharina, Cannabis sativa*, Green Tea, Oak bark, Nettle, *Hamamelis*, Hops, Chamomile, Burdock root, Horsetail, Hawthorn, Lime blossom, Litchi, Almond, Aloe Vera, Spruce needle, Horse chestnut, Sandalwood, juniper, coconut, mango, apricot, lime, wheat, kiwi, melon, orange, grapefruit, sage, rosemary, birch, mallow, cuckooflower, thyme, yarrow, Thyme, lemon balm, cowslip, marshmallow, *Ginseng*, ginger root, *Echinacea purpurea, Olea europea, Boerhavia diffusa* roots, *Foeniculum vulgaris* and *Apim graveolens*. The extracts of *Paeonia lactiflora, Rosa damascena* Flower, *Malus domestica* Fruit, *Argania spinosa* Shell Powder, *Laminaria saccharina, Cannabis sativa*, Green Tea, Nettle, *Hamamelis*, Chamomile, Aloe Vera, *Ginseng, Echinacea purpurea, Olea europea* and/or *Boerhavia diffusa* roots are particularly preferred for use in the compositions according to the present disclosure. Water, alcohols and mixtures thereof may be used as extraction agents for the preparation of the above plant extracts. Among the alcohols, lower alcohols such as ethanol and isopropanol, but especially polyhydric alcohols such as ethylene glycol and propylene glycol, both as the sole extracting agent and mixed with water, are preferred. Plant extracts based on water/propylene glycol in a ratio of 1:10 to 10:1 have proven to be particularly suitable. The plant extracts can be used both in pure and diluted form. If they are used in diluted form, they usually contain approx. about 2-80% by weight of active substance and the extraction agent or mixture of extraction agents used in their extraction as solvent. The plant extracts can be used in the hair treatment compositions according to the present disclosure (based on the total weight of the compositions) preferably in an amount of from about 0.01 to about 10% by weight, more preferably of from about 0.05 to about 7.5% by weight and especially of from about 0.1 to about 5% by weight.

Among suitable pH adjusting agents, particularly preferred for use in the compositions according to the present disclosure are citric acid, lactic acid, malic acid, glycolic acid, especially citric acid and/or lactic acid.

The present disclosure further relates to a solid hair cosmetic composition as described above, with a Shore A hardness value of from about 10 to about 30 and a Shore AO hardness value of from about 5 to about 60.

Such a hardness range is perceived as pleasant by users. In this area it is possible to take a small amount of solid hair cosmetic composition for one application from a jar intended for several applications with the hands and without any other aids.

If a Shore A hardness is indicated in the context of this application, it means that the hardness was determined by measurement with a needle with a truncated conical tip, the face of the truncated cone having a diameter of 1.3 millimetres at an angle of 35°. If a Shore AO hardness is specified, this was measured by measuring with a needle with a spherical segment-shaped rounded tip with a radius of the spherical segment of about 2.5 mm. One durometer was "set" on the product without additional pressure and the maximum value was read. One multiple measurement (at least 3 measurements) was performed in each case and the mean value was given. A manual analogue durometer from Sauter GmbH was used. Unless otherwise expressly described, the instructions enclosed with this device, version 1.2, dated August 2014, which states that it complies with DIN 53505, ASTM D2240 and ISO 868, have been followed.

The present disclosure further relates to a solid hair cosmetic composition as described above for the cleansing and/or care of human skin and/or human hair.

With such a solid hair cosmetic composition the above described benefits can be achieved on human skin and/or human hair.

The present disclosure also relates to a solid hair cosmetic composition as described above for the care of human hair, in particular for use after hair cleansing as a leave-on or rinse-off composition.

The terms 'leave-on' and 'rinse-off' mean that the composition is left in the hair either for a relatively short period of time, such as less than a minute, or for a few minutes or an hour, until it is rinsed out, or that the composition remains in the hair until the next wash, which may be a few days. Both have certain advantages. With a composition that remains on the hair for a long time, the full care potential of all ingredients can be used to a certain extent, whereas a composition that is to be rinsed out again in a short time can also contain ingredients that have a good care effect but whose longer retention in the hair would be unpleasant.

Preferred in terms of the present disclosure are rinse-off compositions.

The present disclosure further relates to a solid hair cosmetic composition as described above in the form of a pen or piece.

As can be seen from the production processes and applications revealed herein, the pen is well suited for multiple use by the user. The present disclosure therefore represents the solid hair cosmetic composition as described above in the form of a multiple use stick.

The piece can be dimensioned in such a way that it can be used either individually or multiple times. Particular preference is given to pieces that are sized to allow the piece to be used only once. The present disclosure therefore provides for the solid hair cosmetic composition as described above in the form of a disposable or reusable piece, preferably in the form of a disposable piece.

These forms of packaging each have certain advantages. One piece still resembles in some ways traditionally used cosmetics and is often preferred by less experimental users. A stick is easier to transport because it is usually fitted with a cap or sleeve and is easier to hold because it can be grasped by its base, sleeve or outer packaging.

As can be seen from the production processes and applications revealed herein, the pen is well suited for multiple use by the user. The present disclosure therefore represents the solid hair cosmetic composition as described above in the form of a multiple use stick.

The piece can be dimensioned in such a way that it can be used either individually or multiple times. Particular preference is given to pieces that are sized to allow the piece to be used only once. The present disclosure therefore provides for the solid hair cosmetic composition as described above in the form of a disposable or reusable piece, preferably in the form of a disposable piece.

A process for preparing the solid hair conditioning composition as previously described, comprising the process:
a) Mix all ingredients with sufficient heat and agitation to ensure that all ingredients are melted and/or evenly distributed,
b) Allow the resulting mixture to cool and solidify.

Such a process makes an evenly mixed solid hair conditioning composition as described above actually available and allows you to experience its benefits.

The present disclosure further relates to a process for preparing the solid hair conditioning composition as previously described, comprising the process:
a) Mix all ingredients with sufficient heat and agitation to ensure that all ingredients are melted and/or evenly distributed,
b) Pour the resulting mixture into a pin/piece mould,
c) Allow the mixture to cool and solidify.

Such a process makes an evenly mixed solid hair conditioning composition in stick or piece form as described above actually available and its related benefits described above can be experienced.

The present disclosure further relates to a process for preparing the solid hair conditioning composition as previously described, comprising the process:
a) Mix all ingredients with sufficient heat and agitation to ensure that all ingredients are melted and/or evenly distributed,
b) Pour the resulting mixture into a mould,
c) Allow the mixture to cool and solidify.

Such a process makes a uniformly blended solid hair conditioning composition actually available in a specific as described above and makes it possible to experience its related benefits described above.

The present disclosure further relates to a process for treating hair, preferably conditioning hair, in which a solid hair cosmetic composition is mixed with water as described above and applied to the hair or in which a pen or piece is applied directly to wet hair and an incorporation is made.

This procedure makes the advantages described above tangible for a user and thus represents an enrichment not only for personal hygiene and care but also a sensory enrichment.

The present disclosure further relates to a use of a solid hair cosmetic composition as described above for treating, preferably conditioning and/or grooming the hair.

This use makes the advantages described above tangible for a user and thus represents an enrichment not only for personal hygiene and care but also a sensory enrichment.

As can be seen from these described designs and their advantages, the process and packaging aspects are important for the present disclosure. They are discussed in more detail below.

In a manufacturing process according to the present disclosure, for example, all ingredients are placed in a heatable container, such as, on a laboratory scale, in a suitable vessel in a water bath or on a heating plate, on a production scale rather in a closed and pressurizable vessel, and are mixed and heated, in the recipes according to the present disclosure, for example at about 75° C., until all ingredients are sufficiently mixed. In such a process, different temperature steps can also be run. For example, components that can be homogeneously mixed even at a relatively low temperature can be mixed first. This can happen at from about 40° C. to about 50° C. It can also be advantageous to mix in certain ingredients at higher temperatures, for example at from about 85° C. to about 90° C. For this purpose, a process according to the present disclosure may comprise one or more steps in this temperature range. Afterwards, one or more steps can be carried out at a lower temperature again, in which further components are mixed in. Typically, the compositions according to the present disclosure solidify at about 65° C., so that certain process steps, such as mixing and extruding the finished mixtures, are not reasonably possible below such a temperature level.

If a composition according to the present disclosure is extruded, the available shape can be determined by a shape of the die closing the extruder. The solidifying mixture can be filled into moulds, portioned on a base or produced endlessly and cut and portioned at the nozzle or afterwards.

It is also important to note that cosmetic products have a lot to do with feeling, fun and emotions. Many people relax during personal hygiene and enjoy the pleasant feeling of doing something good for themselves. Especially since many people find their everyday life more and more demanding or stressful, small pleasures and playfulness are an important point at which stress can be released from a person and satisfaction can be created. Solid cosmetic preparations with incorporated gas phase, i.e. to a certain extent solid foams, feel different from conventional products, which is perceived as interesting and pleasant.

The compositions according to the present disclosure are also suitable for some other forms of packaging not yet described in detail. For example, a stick or pen can be realized. One end of the pen may remain in a wrapper or package during use, so that a user does not have the problem of holding on to a slippery piece of solid cosmetic preparation. The design can be chosen, for example, like a shaving soap, where there is usually a fixed base on one side of the pen and the pen itself is surrounded by a sleeve that can be easily removed by hand, or it can be more similar to a deodorant stick, i.e. include a fixed sleeve also around the outer circumferential surface of the pen as well as a mechanism to gradually advance the pen inside the sleeve so that it always protrudes slightly beyond the opening until it is finally completely worn away by repeated use. The packaging for transport, for example during a journey, is also quite simple with a pen, as a cap surrounding or covering the pen can easily be attached. Pens would be problematic with a conventional conditioner formulation because the material removal on the relatively small surface would be too slow. With the compositions according to the present disclosure, they can be easily realized and the speed of material removal during application meets the expectations of the users without, on the other hand, leading to wasteful use through excessive removal.

The extrusion processes described above can also be used to produce interesting shapes reminiscent of injection-moulded biscuits. Thanks to specially shaped dies on the extrusion die, a variety of shapes can be realized, for example a heart or clover shape. An extruded strand thus obtained can then be cut into pieces or slices, providing emotionally appealing small portions of the solid cosmetic compositions according to the present disclosure. Similarly, it is possible to roll out an extruded strand or other form of a composition according to the present disclosure and then, by punching or cutting, produce pieces that are similar to cookie cutters in terms of shaping properties.

It is also possible to pour the solid cosmetic compositions according to the present disclosure into a crucible, for example a glass jar. Since the strength of these compositions is in a range that allows an application portion to be taken manually, without a tool, from a crucible intended for multiple applications. If the composition has been foamed in a crucible during its manufacture, the result is a particularly interesting feeling.

It is also possible to make up solid cosmetic compositions reminiscent of a piece of paper, a foil or a wafer, which brings with it a new and pleasant feeling during application. Since the layer thickness is small in such a packaging, short dissolution times can be achieved, impatient users are accommodated, sand wasteful use of water does not favour. A product packaged in this way may be placed on the market in a packaging unit in which a large number of leaves or flakes are placed in a small carton, possibly subdivided, so that a single withdrawal is possible.

After various designs and their respective advantages were explained in detail, the presentation of exemplary compositions and an exemplary manufacturing process follows.

Detailed exemplary compositions are shown in the following table 1:

TABLE 1

| Group | Ingredients | Active substances contained therein | A | B |
|---|---|---|---|---|
| 1 | Water | Water | 18 | 36.5 |
| 1 | Citric acid monohydrate | Citric acid | 0.25 | 0.25 |
| 1 | Dehyquart A CA ® | Cetrimonium chloride | 8 | 8 |
| 1 | Glycerine 99.5% | Glycerine | 35 | 35 |
| 1 | Cetearyl alcohol | Cetearyl alcohol | 5 | 2 |
| 1 | Cutina FS 45 | Palmitic acid, stearic acid | 5 | 2 |
| 1 | Cutina GMS-V | Glyceryl stearate | 5 | 2.5 |
| 2 | Agenamalt ® 20.225 Maltodextrin DE15 | Maltodextrin | 1 | 1 |
| 3a | Structure XL ® (28-030A) | Hydroxypropyl starch phosphate | 1.5 | 1.5 |
| 3b | Maisita 9040 ® | *Zea Mays-* (Corn-) starch | 17.25 | 10 |
| 4 | Cetiol SB 45 ® | *Butyrospermum Parkii* (Shea) Butter | 0.5 | 0.5 |
| 4 | Apricot kernel oil, cold pressed | *Prunus Armeniaca* (apricot) seed oil | 2 | 2 |
| 4 | Perfume Tea Grandiosa 611084 | Perfume (Scent) | 0.5 | 0.5 |
| 4 | Phenoxyethanol, pure | Phenoxyethanol | 1 | 1 |

The exemplary procedure was carried out as follows:

The ingredients were used in the ratio shown in the table above. Dehyquart A CA was heated in a drum to 40° C. to 50° C. and, in case of an uneven distribution of its ingredients, mixed. After mixing until homogeneity, the other ingredients of group 1 (see table 2) were added. It was mixed again until homogeneity and then the temperature was increased to 85° C. to 90° C. At this temperature, the ingredients of Group 2 (see Table 2) were added and mixed in until homogeneous. This was then repeated with the ingredients of Group 3 (3a and 3b, see Table 2). The ingredients of Group 4 (see Table 2) were homogeneously mixed together and also added to the previously prepared mixture and mixed in until homogeneity was achieved. After that, the temperature was no longer actively maintained at 85° C. to 90° C., but it was only ensured that it did not drop to 70° C. or less. Finally, the mixture was kept at a temperature above 70° C. for filling or packaging. Finally, the mixture was kept at a temperature above 70° C. for filling or packaging. Finally, the mixture was kept at a temperature above 70° C. for filling or packaging. The resulting mixture was then poured into a pin/piece mould. The mixture was then allowed to cool and solidify.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing

What is claimed is:

1. Solid hair cosmetic composition comprising-based on the total weight of the cosmetic composition—
    a) from about 0.1 to about 40.0% by weight of at least one polysaccharide, wherein at least one polysaccharide is starch from corn, rice, potato or tapioca; modified starch; and/or a dextrin, and:
    b) from about 10.0 to about 60.0% by weight of at least one polyhydric alcohol,
    c) from about 0.1 to about 15.0% by weight of at least one cationic surfactant, and
    d) from about 4 to about 15.0% by weight of at least one saturated or unsaturated, branched or unbranched $C_8$-$C_{30}$ alcohol and/or a saturated or unsaturated, branched or unbranched $C_8$-$C_{30}$ carboxylic acid and/or a salt of a saturated or unsaturated, branched or unbranched $C_8$-$C_{30}$ carboxylic acid.

2. Solid hair cosmetic composition according to claim 1, wherein the polysaccharide a) is chosen from a maize starch, maltodextrin and/or a modified starch.

3. A solid hair cosmetic composition according to claim 1, wherein the polysaccharide a) comprises corn starch, maltodextrin and hydroxypropyl starch phosphate.

4. A solid hair cosmetic composition according to claim 1, comprising from about 1 to about 30.0% by weight of the at least one polysaccharide a), based on the total weight of the cosmetic composition.

5. A solid hair cosmetic composition according to claim 1, comprising glycerol as polyhydric alcohol b).

6. A solid hair cosmetic composition according to claim 1, comprising from about 10 to about 50% by weight of at least one polyhydric alcohol b), based on the total weight of the cosmetic composition.

7. A solid hair cosmetic composition according to claim 1, comprising as the at least one cationic surfactant c)—
    cationic surfactant salts chosen from the group consisting of alkylquats, $C_8$-$C_{30}$-alkyl-tri-$C_1$-$C_4$-alkylammonium salts and/or
    the group of quaternary imidazolines.

8. A solid hair cosmetic composition according to claim 1, comprising from about 0.5 to about 10% by weight of the at least one cationic surfactant c), based on the total weight of the cosmetic composition.

9. A solid hair cosmetic composition according to claim 1, comprising as component d)—
    at least one saturated or unsaturated, branched or unbranched $C_8$-$C_{30}$ alcohol, or
    saturated or unsaturated, branched or unbranched $C_8$-$C_{30}$ carboxylic acids and/or their salts, $C_{10}$-$C_{22}$ carboxylic acids and/or their salts and coco acids, lauric acid, myristic acid, palmitic acid, stearic acid, behenic acid, oleic acid and mixtures thereof and/or the salts of these acids.

10. A solid hair cosmetic composition according to claim 1, comprising as component d) at least one saturated or unsaturated, branched or unbranched C8-C30 alcohol.

11. A solid hair cosmetic composition according to claim 1, comprising as component d) cetyl alcohol, stearyl alcohol, or mixtures thereof.

12. A solid hair cosmetic composition according to claim 1, comprising as component d) palmitic acid and/or stearic acid and mixtures thereof, and/or cetyl alcohol and/or stearyl alcohol.

13. A solid hair cosmetic composition according to claim 1, comprising as component d) palmitic acid, stearic acid and cetyl alcohol.

14. A solid hair cosmetic composition according to claim 1, further comprising, based on the total weight of the cosmetic composition, from about 0.01 to about 5.00% by weight of at least one cationic polymer obtainable from guar, *cassia* and/or inulin.

15. Solid hair cosmetic composition according to claim 1 in the form of a pen or piece.

16. A process for preparing the solid hair conditioning composition according to claim 1, comprising the process:
    a) Mix all ingredients with sufficient heat and agitation to ensure that all ingredients are melted and/or evenly distributed,
    b) Allow the resulting mixture to cool and solidify.

17. A process for preparing the solid hair conditioning composition according to claim 1, comprising the process:
    a) Mix all ingredients with sufficient heat and agitation to ensure that all ingredients are melted and/or evenly distributed,
    b) Pour the resulting mixture into a pin/piece mould,
    c) Allow the mixture to cool and solidify.

18. Process for treating hair, conditioning hair, in which a solid hair cosmetic composition according to claim 1 is mixed with water and applied to the hair or in which a stick or piece is applied directly to wet hair and worked in.

19. A solid hair cosmetic composition according to claim 1, wherein
    the polysaccharide is a combination of maltodextrin, hydroxypropyl starch phosphate, and corn starch;
    the polyhydric alcohol is glycerol;
    the cationic surfactant is cetrimonium chloride;
    the at least one alcohol and/or carboxylic acid is a combination of cetearyl alcohol, palmitic acid, and stearic acid, and
    the solid hair cosmetic composition is a piece.

* * * * *